United States Patent [19]

Aeschlimann

[11] Patent Number: 5,155,271
[45] Date of Patent: Oct. 13, 1992

[54] PROCESS FOR THE ALKYLATION OF AROMATIC AMINES

[75] Inventor: Peter Aeschlimann, Allschwil, Switzerland

[73] Assignee: Ciba-Geigy Corporation, Ardsley, N.Y.

[21] Appl. No.: 543,245

[22] Filed: Jun. 25, 1990

[51] Int. Cl.$^5$ .................................. C07C 237/32
[52] U.S. Cl. .......................... 564/176; 544/337; 544/360; 544/391; 546/327; 546/334; 558/29; 558/392; 560/106; 560/250; 560/251; 562/11; 562/29; 564/82; 564/95; 564/97; 564/154; 564/163; 564/167; 564/172; 564/175; 564/177; 564/401; 564/402; 564/428; 564/440
[58] Field of Search ............... 564/401, 440, 82, 163, 564/154, 95, 97, 167, 402, 428, 172, 175, 176, 177; 544/391, 337, 360; 546/327, 334; 558/29, 392; 560/106, 250, 251; 562/11, 29

[56] References Cited

U.S. PATENT DOCUMENTS

| | | | |
|---|---|---|---|
| 2,813,124 | 11/1957 | Rice et al. | 564/401 |
| 4,380,666 | 4/1983 | Gabrielsen et al. | 564/82 |
| 4,612,394 | 9/1986 | Kotera et al. | 564/440 |
| 4,786,721 | 11/1988 | Tzikas et al. | 534/617 |
| 4,841,048 | 6/1989 | Sawamoto et al. | 544/74 |
| 4,929,757 | 5/1990 | Herd | 564/423 |

FOREIGN PATENT DOCUMENTS

| | | |
|---|---|---|
| 0172789 | 2/1986 | European Pat. Off. |
| 0295527 | 12/1988 | European Pat. Off. |
| 2100778 | 3/1972 | France |
| 0140049 | 8/1983 | Japan .................................. 564/401 |
| 1223012 | 2/1971 | United Kingdom ............... 564/82 |
| 1314997 | 4/1973 | United Kingdom |

OTHER PUBLICATIONS

March, *Advanced Organic Chemistry*, pp. 1049, 1093, and 1108 (1985).
Sharp, Ed., *Miall's Dictionary of Chemistry*, p. 440 (1981).
Simov, D et al., "Preparation of benzoxazolonyl alkyl Sulfone, etc", CA 66, 115401m (1967).
Sumitomo Chemical, Co., CA 101, 92781k (1984).
Ainsworth, C., "The Reductive Alkylation of Primary Aromatic Amines w. Raney Ni & Alcohols", JACS, 1635, Apr. 20, 1956.
Rice, R et al, "Raney Nickel Catalyzed N-Alkylation of Aniline etc", JACS, 4052, Aug. 5, 1955.
Vol. 77, Journal of Amer. Chemical Society (1955) pp. 4052–4054.
Organic Chemistry vol. 21 (1956) p. 474.
Wilfred John Hickinbottom, Reactions of Organic Compounds, Longmans, p. 130 (1959).

Primary Examiner—Richard L. Raymond
Assistant Examiner—Scott C. Rand
Attorney, Agent, or Firm—Kevin T. Mansfield; Edward McC. Roberts

[57] ABSTRACT

The invention relates to a process for the preparation of compounds of the formula

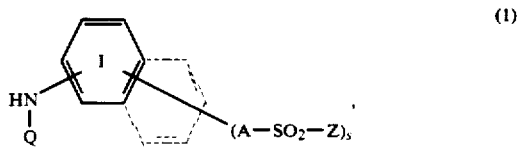
(1)

in which Q is substituted or unsubstituted $C_1$–$C_6$alkyl, A is a direct bond or a bridging member, s is the number 1 or 2, Z is a radical of the formula $-CH_2CH_2OH$, $-CH=CH_2$ or $-CH_2CH_2-Y$, and Y is a leaving group, and the benzene or napthalene nucleus I can be further substituted, which comprises reacting compounds of the formula

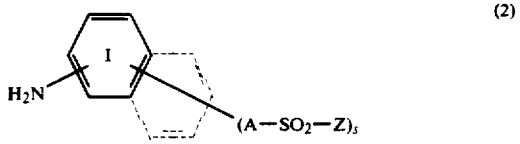
(2)

with compounds of the formula

Q—OH (3)

in which A, s, Z and Q are as defined under formula (1), in the presence of hydrogenation catalysts, and then carrying out further conversion reactions where appropriate.

The compounds obtained by the process according to the invention are suitable as intermediates for the preparation of reactive dyes.

16 Claims, No Drawings

PROCESS FOR THE ALKYLATION OF AROMATIC AMINES

The invention relates to a novel process for the preparation of N-alkylated aromatic amines which contain a β-hydroxyethylsulfonyl radical, from the corresponding non-alkylated amines, by alkylating the amino group with an alcohol in the presence of hydrogenation catalysts.

Many processes for the preparation of monoalkylated aromatic amines are disclosed in the literature. Most of the methods of alkylation have the disadvantages that the yield is unsatisfactory and the selectivity in the preparation of monoalkylated products is low.

Surprisingly, the process according to the invention makes it possible to prepare N-monoalkylated aromatic amines which contain a β-hydroxyethylsulfonyl radical from the corresponding non-alkylated amines in a straightforward manner without the said disadvantages.

Thus the invention relates to a process for the preparation of compounds of the formula

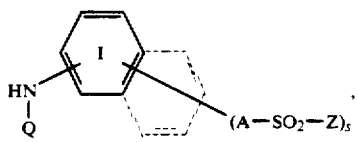  (1)

in which Q is substituted or unsubstituted $C_1$–$C_6$alkyl, A is a direct bond or a bridging member, s is the number 1 or 2, Z is a radical of the formula —$CH_2CH_2OH$, —$CH=CH_2$ or —$CH_2CH_2$—Y, and Y is a leaving group, and the benzene or naphthalene nucleus I can be further substituted, which comprises reacting compounds of the formula

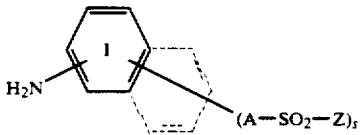  (2)

with compounds of the formula

Q—OH  (3)

in which A, s, Z and Q are as defined under formula (1), in the presence of hydrogenation catalysts, and then carrying out further conversion reactions where appropriate.

Surprisingly, this process yields N-monoalkylated aromatic amines of the formula (1) in a purity of more than 90%. Furthermore, the compounds of the formula (1) are obtained in higher yields than by processes customary hitherto.

The amines of the formula (2) used in the process according to the invention are either aniline derivatives or naphthylamine derivatives of the formulae

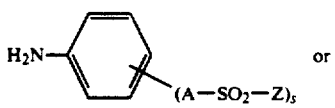 or

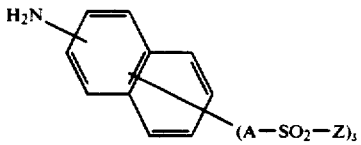

where the benzene nucleus or the naphthalene nucleus can be further substituted, and A, s and Z are as defined under formula (1). Examples of suitable substituents for the benzene nucleus or the naphthalene nucleus are the following: $C_1$–$C_4$alkyl such as methyl, ethyl, propyl, isopropyl, butyl, isobutyl, sec-butyl and tert-butyl, $C_1$–$C_4$alkoxy such as methoxy, ethoxy, propoxy, isopropoxy, sec-butoxy, tert-butoxy, isobutoxy and n-butoxy, halogen such as fluorine, chlorine and bromine, and sulfo. Preferred substituents are methyl, ethyl, methoxy, ethoxy, chlorine, bromine and sulfo; these substituents are bonded, in particular, to the benzene nucleus. The naphthalene nucleus is preferably unsubstituted or substituted by a sulfo group.

Examples of suitable $C_1$–$C_6$alkyl for Q are: methyl, ethyl, n-propyl, isobutyl, sec-butyl, n-butyl, n-pentyl and n-hexyl, and the corresponding radicals which can be substituted, for example by hydroxyl, cyano, $C_1$–$C_4$alkoxy, for example methoxy, ethoxy, isopropoxy, propoxy and n-butoxy, halogen such as fluorine, chlorine and bromine, carboxyl, carbamoyl, $C_1$–$C_4$alkoxycarbonyl such as methoxycarbonyl and ethoxycarbonyl, $C_1$–$C_4$alkylcarbonyloxy such as acetyloxy, sulfo and sulfamoyl. Examples of radicals substituted in this way which may be mentioned are: 2-hydroxyethyl, 2-hydroxypropyl, 3-hydroxypropyl, 2-hydroxybutyl, 3-hydroxybutyl, 4-hydroxybutyl, 2,3-dihydroxypropyl, 2,4-dihydroxybutyl, cyanomethyl, 2-cyanoethyl, 3-cyanopropyl, methoxymethyl, ethoxymethyl, 2-methoxyethyl, 2-ethoxyethyl, 3-methoxypropyl, 3-ethoxypropyl, 2-hydroxy-3-methoxypropyl, chloromethyl, 2-chloroethyl, 2-bromoethyl, bromomethyl, 3-chloropropyl, 4-chlorobutyl, carboxymethyl, 2-carboxyethyl, 3-carboxypropyl, 4-carboxybutyl, 1,2-dicarboxyethyl, carbamoylmethyl, 2-carbamoylethyl, 3-carbamoylpropyl, methoxycarbonylmethyl, 2-methoxycarbonylethyl, 4-methoxycarbonylbutyl, 4-ethoxycarbonylbutyl, methylcarbonyloxymethyl, 3-methylcarbonyloxypropyl, 3-ethylcarbonyloxypropyl, 4-methylcarbonyloxybutyl, sulfomethyl, 2-sulfoethyl, 2-sulfopropyl, sulfamoylmethyl, 2-sulfamoylethyl.

Examples of suitable bridging members A are the following radicals: —($CH_2$)—$_{1-2}$ and in particular —$CON(R_3)$—($CH_2$)$_m$—, —(O)—$_{0-1}CH_2$—$CON(R_3)$—($CH_2$)$_m$— or —$N(R_3)$—, for example —$CONHCH_2CH_2$—, —$CH_2CONHCH_2CH_2$—, —$OCH_2CONHCH_2CH_2$— and —$N(H)$—, where $R_3$ is hydrogen, methyl or ethyl, and m is 2, 3, 4, 5 or 6. If A is a bridging member, the radical —$SO_2Z$ is bonded to the $CH_2$ group of the said radicals or to the nitrogen atom in the radical —$N(R_3)$—.

Y is, for example, an inorganic or organic radical which can be eliminated under alkaline conditions.

Examples of suitable Y radicals are:

—$OSO_3H$, —$SSO_3H$, —$OCOCH_3$, —$OCO$—$C_6H_5$, $OPO_3H_2$, —Cl, —Br, —F,

-continued

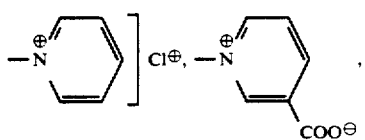

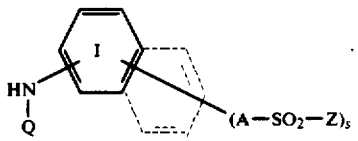

Y is preferably the group —OSO₃H, —OCOCH₃, —O-PO₃H₂ or —Cl. Suitable numbers for s are 1 and 2. s is preferably the number 1.

A preferred embodiment of the process according to the invention comprises using as compounds of the formula (2) compounds of the formula (2a)

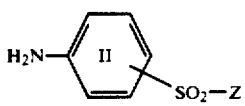 (2a)

in which Z is as defined under formula (1), and the benzene nucleus II can contain further substituents.

Another preferred embodiment of the process according to the invention comprises using compounds of the formula

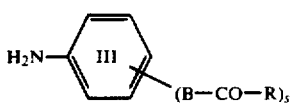 (2b)

in which s is as defined under formula (1), B is a direct bond or a radical of the formula —CH₂)ₙ or —O—CH₂)ₙ, n is 1 to 6, R is a radical of the formula

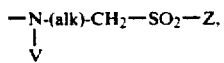 (4a)

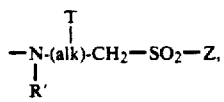 (4b)

—N—(CH₂)ₚ—O—(CH₂)_q—SO₂—Z, (4c)
|
R'

—N—(CH₂)ₚ—NH—(CH₂)_q—SO₂—Z, (4d)
|
R'

—N—(CH₂)ₚ—N[(CH₂)_q—SO₂—Z]₂ or (4e)
|
R'

(4f)

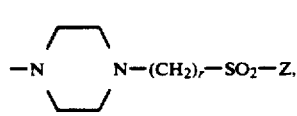

in which R' is hydrogen or C₁-C₆alkyl, (alk) is a C₁-C₆alkylene radical, T is hydrogen, halogen, hydroxyl, sulfato, carboxyl, cyano, C₁-C₄alkoxycarbonyl, carbamoyl or a radical —SO₂—Z, V is hydrogen, substituted or unsubstituted C₁-C₄alkyl or a radical of the formula —(alk)—CH₂—SO₂—Z in which (alk) is as defined above, Z is as defined under formula (1), and p, q and r are, independently of one another, an integer from 1 to 6, and the benzene nucleus III can contain further substituents. In the formula (2b) s is, in particular, the number 1.

Examples of R' in the formulae (4b) to (4e) are hydrogen, methyl, ethyl, n- or iso-propyl, n-, sec- or tert-butyl or a straight-chain or branched pentyl or hexyl radical. R' is preferably hydrogen, methyl or ethyl, and particularly preferably hydrogen.

Examples of (alk), for example in formulae (4a) and (4b) are a methylene, ethylene, 1,3-propylene, 1,4-butylene, 1,5-pentylene and 1,6-hexylene radical or its branched isomers. The preferred meaning for (alk) is a C₁-C₄alkylene radical, and the particularly preferred meaning is methylene or ethylene.

In the formulae (4c), (4d) and (4e) p and q are, independently of one another, preferably an integer from 1 to 4; p and q are each particularly preferably the number 2.

T is preferably hydrogen, hydroxyl, sulfato, acetyloxy, carboxyl, methoxycarbonyl, ethoxycarbonyl or the group —SO₂—Z, where Z is as defined above; T is particularly preferably hydrogen or a radical —SO₂—Z.

If V is a substituted C₁-C₄alkyl radical, this can be substituted by, for example, halogen, hydroxyl, cyano, carboxyl, sulfo, sulfato, C₁-C₄alkoxy or C₁-C₄alkoxycarbonyl.

Examples of substituted C₁-C₄alkyl radicals are: carboxymethyl, β-carboxyethyl, methoxycarbonylmethyl, ethoxycarbonylmethyl, β-carboxyethyl, methoxycarbonylmethyl, ethoxycarbonylmethyl, β-methoxyethyl, β-ethoxyethyl, β-chloroethyl, γ-bromopropyl, β-hydroxyethyl, β-hydroxybutyl, β-cyanoethyl, sulfomethyl, β-sulfoethyl, β-sulfatoethyl.

If V is a radical of the formula Z—O₂S—H₂C—(alk)—, this can differ from or, preferably, be identical to the second radical Z—O₂S—H₂C—(alk)— present in the formula (4a).

V is preferably hydrogen, methyl, ethyl or the group Z—O₂S—H₂C(alk)—; V particularly preferably has the meaning of hydrogen.

Examples of particularly preferred R radicals are:

—NH—(CH₂)₂—SO₂—(CH₂)₂—OSO₃H,

—NH—(CH₂)₂—SO₂—(CH₂)₂—OH

—NH—(CH₂)₃—SO₂—(CH₂)₂—OSO₃H,

—NH—(CH₂)₃—SO₂—(CH₂)₂—OH

—NH—(CH₂)₂—O—(CH₂)₂—SO₂—(CH₂)₂—OSO₃H,

—NH—(CH₂)₂—O—(CH₂)₂—SO₂—(CH₂)₂—OH

—N[—(CH₂)₂—SO₂—(CH₂)₂—OSO₃H]₂,

—N[—(CH₂)₂—SO₂—(CH₂)₂—OH]₂

—N—(CH₂)₂—SO₂—(CH₂)₂—OSO₃H,
|
CH₃

—N—(CH₂)₂—SO₂—(CH₂)₂—OH
|
CH₃

-continued

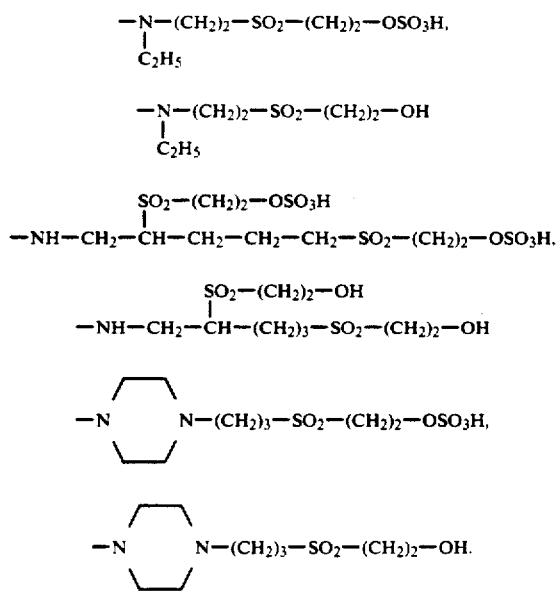

The process according to the invention starts, in particular, from compounds of the formula (2) or (2a) or (2b) whose benzene nucleus or naphthalene nucleus contains no further substituents apart from the $H_2N$ group and the radical $-A-SO_2-Z$.

A particularly preferred embodiment of the process according to the invention comprises using compounds of the formula (3) in which Q is $C_1-C_4$alkyl, especially ethyl.

A very particularly preferred embodiment of the process according to the invention comprises using compounds of the formula (2), (2a) or (2b) in which Z is β-hydroxyethyl, β-sulfatoethyl, β-thiosulfatoethyl, β-phosphatoethyl, β-acetoxyethyl, β-halogenoethyl or vinyl. Compounds of the formula (2), (2a) or (2b) in which Z is β-hydroxyethyl are particularly used. The conversion of the radical Z as β-hydroxyethyl into another abovementioned radical Z takes place, in particular, after the alkylation.

An important embodiment of the process according to the invention for the preparation of compounds of the formula

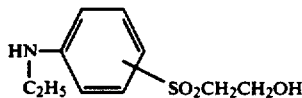

(5)

comprises reacting compounds of the formula

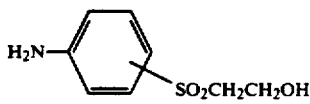

(6)

with ethanol in the presence of Raney nickel.

Another important embodiment of the process according to the invention for the preparation of compounds of the formula

(7)

comprises reacting compounds of the formula

(8)

with ethanol in the presence of Raney nickel.

The process according to the invention is carried out in the presence of hydrogenation catalysts. Particularly suitable hydrogenation catalysts are noble metal catalysts, for example platinum, palladium, nickel and copper chromite catalysts. The required reaction temperature essentially depends on the catalyst used. Reaction temperatures between 50° and 250° C. have proved beneficial, and the reaction is preferably carried out at a temperature between 100° and 160° C., in particular between 120° and 140° C., in which case a nickel catalyst has proved particularly suitable as hydrogenation catalyst. Raney nickel is very particularly preferably employed as hydrogenation catalyst in the process according to the invention. The reaction can be carried out under atmospheric pressure or superatmospheric pressure. If the reaction is carried out under superatmospheric pressure, the superatmospheric pressure is generally between 1 and 6 bar, in particular between 2.5 and 4.5 bar. The process according to the invention is preferably carried out under anhydrous conditions. The reaction time essentially depends on the activity of the hydrogenation catalyst, in particular Raney nickel.

A preferred embodiment of the process according to the invention comprises alkylating the compound of the formula (3) in the presence of Raney nickel under atmospheric pressure at the reflux temperature.

A likewise preferred embodiment of the process according to the invention comprises reacting compounds of the formula (6) or (8) with ethanol in the presence of Raney nickel at temperatures between 120° and 140° C. under a maximum superatmospheric pressure of 4 bar. The $-NH_2$ group in the compounds of the formula (4) or (8) is preferably in the m or p position.

The compounds of the formula (1) obtained according to the invention, in which Z is β-hydroxyethyl, can be converted into other compounds of the formula (1), i.e. the alkylation of the compound of the formula (2) in which Z is β-hydroxyethyl is followed, where appropriate, by a conversion reaction, for example an esterification or dehydration.

Thus, compounds of the formula (1) in which the group $-SO_2-Z$ is a β-hydroxyethylsulfonyl group can be converted by treatment with sulfating agents, phosphorylating agents, halogenating agents, alkyl- or arylsulfonyl halides, alkyl- or arylcarbonyl halides or alkyl- or arylcarboxylic anhydrides to the corresponding products in which the group $-SO_2-Z$ is, for example the group $-SO_2-CH_2-CH_2-O-SO_3H$, $-SO_2-CH_2-CH_2-O-PO_3H_2$, $-SO_2-CH_2-CH_2-$halogen, $-SO_2-CH_2-CH_2-O-CO-CH_3$ or $-SO_2-CH_2-CH_2-O-CO-C_2H_5$. The products obtained in this way can in turn be converted by treatment with alkaline agents, for example alkali metal hydroxide or alkali metal carbonate, such as sodium hydroxide or sodium carbonate, into corresponding compounds in which the group —SO$_2$—Z is the group —SO$_2$—CH=CH$_2$. The products obtained in this way can in turn be converted by reaction (addition) with salts of thiosulfuric acid such as sodium thiosulfate into compounds in which the group —SO$_2$—Z is the group —SO$_2$—CH$_2$—CH$_2$—S—SO$_3$H.

Examples of sulfating agents suitable for this are concentrated sulfuric acid, and chlorosulfonic acid and amidosulfonic acid or other compounds providing sulfur trioxide. Examples of phosphorylating agents suitable for this are concentrated phosphoric acid, alkyl pyro-, meta- or polyphosphates, phosphorus oxychloride or mixtures of phosphoric acid and phosphorus(V) oxide. Examples of halogenating agents which can be used are thionyl chloride and thionyl bromide.

The hydroxyl group in a compound of the formula (1) is sulfated, for example, by reaction with concentrated sulfuric acid at 0° C. to a moderately elevated temperature. The sulfation can also be carried out by reacting the hydroxyl compound with two equivalents of chlorosulfonic acid per hydroxyl group in a polar organic solvent, for example N-methylpyrrolidone, at 10° to 80° C. The sulfation is preferably carried out by introducing the relevant compound into sulfuric acid monohydrate at temperatures between 5° and 15° C. The introduction of another radical for Z in a compound of the formula (1) in place of a halogen atom or the sulfato group, for example a thiosulfato or phosphato group, is carried out in a manner known per se.

Thus the present invention also relates to a process for the preparation of compounds of the formula

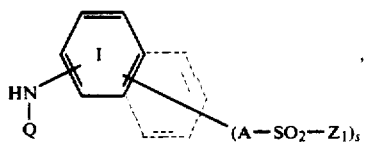

(9)

in which Q, s and A are as defined under formula (1), Z$_1$ is a radical of the formula —CH=CH$_2$ or —CH$_2$CH$_2$—Y, and Y is a leaving group, and the benzene and naphthalene nucleus I can be further substituted, which comprises reacting compounds of the formula

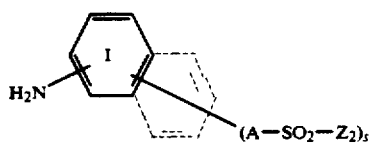

(10)

with compounds of the formula

Q—OH (3)

in which A, s and Q are as defined under formula (1), and Z$_2$ is the radical of the formula —CH$_2$CH$_2$OH, in the presence of hydrogenation catalysts, and subsequently converting the radical Z$_2$ into a radical Z$_1$, the conversion being carried out as indicated above. The preferences applying to the preparation of the compound of the formula (9) from the compound of the formula (10) are the same as indicated for the preparation of the compound of the formula (1).

A preferred embodiment of the process according to the invention comprises reacting compounds of the formula

(7)

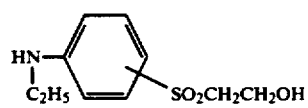

(5)

with sulfating agents.

Sulfating agents which have proved particularly suitable are concentrated sulfuric acid or chlorosulfonic acid in a polar organic solvent, or sulfamic acid, in particular in N-methylpyrrolidone.

Examples of compounds of the formula (2) which may be mentioned are:

3-(β-hydroxyethylsulfonyl)aniline, 4-(β-hydroxyethylsulfonyl)aniline, 2-(β-hydroxyethylsulfonyl)aniline, 3-aminobenzoic acid N-[β-(β-hydroxyethylsulfonyl)ethyl]amide, 4-aminobenzoic acid N-[β-(β-hydroxyethylsulfonyl)ethyl]amide.

Examples of compounds of the formula (3) which may be mentioned are: methanol, ethanol, n-propanol, n-butanol, n-pentanol, n-hexanol.

The compounds of the formula (2) in which A is a direct bond and which are, for example, of the formula (2a) are known and can be obtained in a manner known per se.

The compounds of the formula (2) in which A is a bridging member and which are, for example, of the formula (2b) can be prepared in a manner known per se, for example by initially reacting a compound of the formula

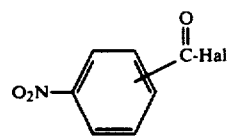

(11)

in which Hal is halogen, in particular chlorine, with an amine of the formula

NH-(alk)-CH$_2$—SO$_2$—Z
|
V (4a$_1$)

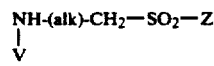

(4b$_1$)

NH—(CH$_2$)$_p$—O—(CH$_2$)$_q$—SO$_2$—Z
|
R'

(4c$_1$)

NH—(CH$_2$)$_p$—NH—(CH$_2$)$_q$—SO$_2$—Z
|
R'

(4d$_1$)

$$\text{NH}-(\text{CH}_2)_p-\text{N}[(\text{CH}_2)_q-\text{SO}_2-\text{Z}]_2 \text{ or} \quad (4e_1)$$
$$|$$
$$\text{R}'$$

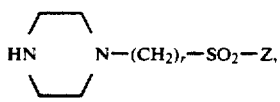 (4f₁)

in which (alk), V, T, R', p, q, r and Z are each as defined above, in particular Z being β-hydroxyethyl, reducing the nitro group to the amino group, and converting the radical Z into another radical Z where appropriate.

As a modification of the process described above, it is also possible to use in place of the nitro compound of the formula (11) the corresponding amino compound, and thus the nitro group reduction step is dispensed with. The nitro compounds of the formula (11), as well as the corresponding amino compounds, are known per se or can be obtained by known methods.

Another variant of the process described above comprises employing suitable precursors in place of the amines of the formulae (4a₁) to (4f₁), and subsequently converting them into the corresponding amines.

Examples of suitable precursors are the thioether amines which are analogous to the formulae (4a₁) to (4f₁) and which can be oxidized in a known manner to the corresponding sulfones after the reaction with a compound of the formula (11).

It is possible initially to react suitable halogenoalkylamines with the acid chloride of the formula (11) and to react the compounds resulting from this with 2-mercaptoethanol and sodium alcoholate in alcohol to give the abovementioned thioether amines, which can in turn be subsequently oxidized to the sulfones of the formulae (4a₁) to (4f₁).

It is preferable to employ those amines of the formulae (4a₁) to (4f₁), or precursors thereof, which contain a precursor of the reactive radical and, accordingly, Z is, for example, a radical of the formula HO—H₂C—H₂C—. The precursor of the reaction radical is then subsequently converted into the final stage as described hereinbefore.

The amines of the formulae (4a₁) to (4f₁) and precursors thereof are disclosed, for example, in EP-A 210 951 or can be prepared in analogy thereto.

The reaction (condensation) of the acid chloride of the formula (11) with the abovementioned amines is carried out, for example, in aqueous, aqueous-organic or organic medium at a temperature between 0° C. and 120° C., preferably 10° to 60° C., in the presence of alkaline acid-binding agents, for example alkali metal hydroxides, carbonates or bicarbonates.

If precursors of the amines of the formulae (4a₁) to (4f₁) are used as starting materials, the oxidation of the thioether compounds to the sulfones can be carried out by various methods, for example with hydrogen peroxide with or without the addition of tungsten or vanadium compounds as catalysts, furthermore with peracetic acid, potassium permanganate or chromic acid, or with chlorine/hydrochloric acid, in each case in aqueous, aqueous-organic or organic medium.

The nitro group is reduced to the amino group in a manner known per se by catalytic hydrogenation with Pd/carbon in ethanol, ethyl acetate or tetrahydrofuran at room temperature to about 40° C. The reduction can also be carried out with Fe/acetic acid in aqueous solution.

The carboxamides which can be obtained in this way and in which the —SO₂—Z group is a β-hydroxyethylsulfonyl group can be converted by treatment with sulfating agents, phosphorylating agents, halogenating agents, alkyl- or arylsulfonyl halides, alkyl- or arylcarbonyl halides or alkyl- or arylcarboxylic anhydrides into the corresponding products in which the —SO₂—Z group is, for example, the —SO₂—CH₂—CH₂—O—SO₃H, —SO₂—CH₂—CH₂—O—PO₃H₂, —SO₂—CH₂—CH₂-halogen, —SO₂—CH₂—CH₂—O—CO—CH₃ or —SO₂—CH₂—CH₂—O—CO—C₂H₅ group. The products obtained in this way can in turn be converted by treatment with alkaline agents, for example alkali metal hydroxide or alkali metal carbonate, such as sodium hydroxide or sodium carbonate, into corresponding compounds in which the —SO₂—Z group is the —SO₂—CH=CH₂ group. The products obtained in this way can in turn be converted by reaction (addition) with salts of thiosulfuric acid, such as sodium thiosulfate, into compounds in which the —SO₂—Z group is the —SO₂—CH₂—CH₂—S—SO₃H group.

The compounds of the formula (1) obtained according to the invention are suitable as intermediates for the preparation of reactive dyes, by, for example for the preparation of bireactive dyes, condensing a compound of the formula (1) in which Z is, for example, vinyl with a trihalogeno-s-triazine, and reacting the resulting dihalogeno-s-triazine compound with an amino-containing chromophore to give a reactive dye with a monohalogeno-s-triazine residue.

The process according to the invention has the following advantages over known processes for the preparation of compounds of the formula (1):

The reaction can be more quantitative than hitherto possible owing to the selective monoalkylation of the aromatic amines of the formula (2) with the alkylating agent in the presence of hydrogenation catalysts.

Reactive dyes with reproducibly improved properties, in particular better solubility in water, can be obtained owing to the higher purity of the compounds obtained by the process according to the invention compared with the same compounds prepared by conventional means.

The examples which follow serve to illustrate the invention. The parts and percentages therein are by weight. The temperatures are indicated in degrees Celsius. The relation between parts by weight and parts by volume is the same as that between grammes and cubic centimetres.

EXAMPLE 1

136 parts of the compound of the formula

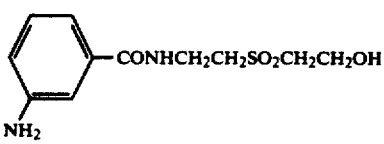 (100)

are suspended in 1000 parts of ethanol together with 50 parts of Raney nickel in ethanol and stirred in a steel autoclave at 125° for 24 hours, during which the maximum pressure is about 4 bar. The reaction mixture is subsequently filtered to remove Raney nickel and cooled in an ice bath. The reaction product of the formula

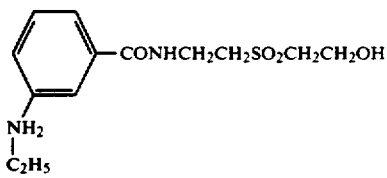
(101)

precipitates as a white mass and is filtered off cold. The residue is washed with cold ethanol, pressed dry and then dried. The yields is 117 parts (77% of theory). The purity of monoethylated product is 92%.

EXAMPLE 2

100.5 parts of the compound of the formula

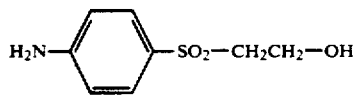
(102)

are stirred in 1500 parts of ethanol together with 50 parts of Raney nickel in ethanolic suspension in a steel autoclave at 135° C. for 36 hours. The Raney nickel is subsequently filtered off, and the filtrate is evaporated to dryness. 110 parts of the compound of the formula

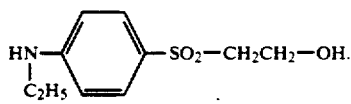
(103)

are obtained. The purity of monoethylated product is 94%.

The above procedure is repeated using an equimolar amount of 2-amino-6-(β-hydroxyethylsulfonyl)naphthalene in place of the compound of the formula (102), resulting in 2-(N-ethylamino)-6-(β-hydroxyethylsulfonyl)naphthalene as reaction product.

EXAMPLE 3

136 parts of the compound of the formula

(104)

are stirred in 1000 parts of ethanol with 50 parts of Raney nickel in ethanolic suspension at 135° C. for 48 hours. The Raney nickel is subsequently filtered off, and the reaction product is cooled. The reaction product of the formula

(105)

precipitates as a white mass and is filtered off cold. The residue is washed with cold ethanol, pressed dry and then dried. The resulting product has a purity of monoethylated product of 90%.

EXAMPLE 4

Sulfation of the compound of the formula (101) from Example 1. 60 parts of the isolated and dried compound of the formula (101) are stirred together with 29.1 parts of sulfamic acid into 45 parts of N-methylpyrrolidone and stirred at a temperature of 75°-80° C. for three hours. Sulfation takes place quantitatively. The reaction product has, in the form of the free acid, the formula

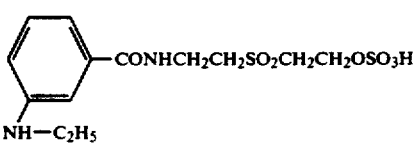
(106)

The reaction product of the formula (106) can be employed without isolation in subsequent stages.

EXAMPLE 5

Sulfation of the compound of the formula (103) from Example 2. 18.4 parts of the dried compound of the formula (103) are introduced at 5°-10° C. into 90 parts of oleum (25% strength). The temperature is raised to 50° C. and the mixture is stirred for one hour.

The clear reaction solution is homogeneous and free of starting material.

It is now discharged at 0° C. onto ice, and the pH is adjusted to 1.5 with 90 parts of $CaCO_3$ and then to pH 5 with sodium carbonate solution. The calcium sulfate is filtered off and then the mother liquor is evaporated to dryness. The reaction product has, in the form of the free acid, the formula

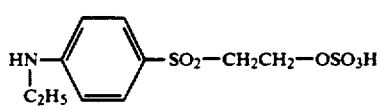
(107)

The procedures indicated in Examples 1 to 3 are repeated, reacting in place of the compounds of the formulae (100), (102) and (104) an equimolar amount of a compound of the formula

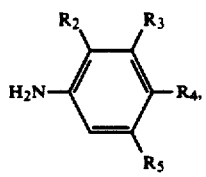
(108)

in which $R_2$, $R_3$, $R_4$ and $R_5$ have the meanings indicated in the following table, in an alcohol of the formula

Q—OH  (109), in which Q has the meaning indicated in the following table, in the presence of Raney nickel at 130°-140° C. for 10 to 20 hours and under a pressure between 2 to 6 bar, resulting in compounds of the formula

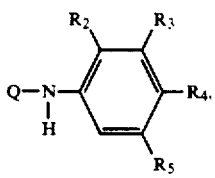

(110)

in which $R_2$, $R_3$, $R_4$, $R_5$ and Q have the meanings indicated in the following table.

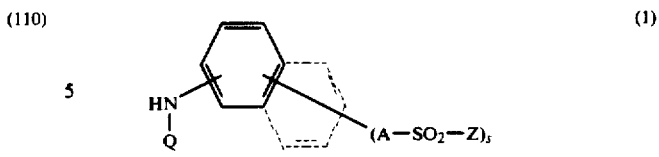

(1)

in which Q is $C_1$-$C_6$alkyl, A is a direct bond $-(CH_2)_{1-2}-$, $-CON(R_3)-(CH_2)_m-$, $-(O)_{0-1}-CH_2-CON(R_3)-(CH_2)_m-$ or $-N(R_3)-$, where $R_3$ is

TABLE

| Example | $R_2$ | $R_3$ |
|---|---|---|
| 6 | —H | —SO$_2$CH$_2$CH$_2$OH |
| 7 | —H | —SO$_2$CH$_2$CH$_2$OH |
| 8 | —H | —SO$_2$CH$_2$CH$_2$OH |
| 9 | —H | —H |
| 10 | —H | —H |
| 11 | —SO$_2$CH$_2$CH$_2$OH | —H |
| 12 | —CONH(CH$_2$)$_2$SO$_2$CH$_2$CH$_2$OH | —H |
| 13 | —CONH(CH$_2$)$_2$SO$_2$CH$_2$CH$_2$OH | —H |
| 14 | —CONH(CH$_2$)$_2$SO$_2$CH$_2$CH$_2$OH | —H |
| 15 | —H | —H |
| 16 | —H | —H |
| 17 | —H | —CONH(CH$_2$)$_2$SO$_2$CH$_2$CH$_2$OH |
| 18 | —H | —CONH(CH$_2$)$_2$SO$_2$CH$_2$CH$_2$OH |
| 19 | —CH$_3$ | —H |
| 20 | —Cl | —H |
| 21 | —CH$_3$ | —H |
| 22 | —H | —CON(CH$_2$CH$_2$SO$_2$CH$_2$CH$_2$OH)$_2$ |
| 23 | —H | —CON(CH$_2$CH$_2$SO$_2$CH$_2$CH$_2$OH)$_2$ |
| 24 | —H | —H |
| 25 | —H | —H |
| 26 | —H | —OCH$_2$CONHCH$_2$CH$_2$SO$_2$CH$_2$CH$_2$OH |
| 27 | —H | —CH$_2$SO$_2$CH$_2$CH$_2$OH |
| 28 | —H | —CH$_2$SO$_2$CH$_2$CH$_2$OH |
| 29 | —H | —CH$_2$CH$_2$SO$_2$CH$_2$CH$_2$OH |
| 30 | —H | —H |

| Example | $R_4$ | $R_5$ | Q |
|---|---|---|---|
| 6 | —H | —H | —C$_2$H$_5$ |
| 7 | —H | —H | n-C$_3$H$_7$ |
| 8 | —H | —H | n-C$_4$H$_9$ |
| 9 | —SO$_2$CH$_2$CH$_2$OH | —H | n-C$_3$H$_7$ |
| 10 | —SO$_2$CH$_2$CH$_2$OH | —H | n-C$_4$H$_9$ |
| 11 | —H | —H | —C$_2$H$_5$ |
| 12 | —H | —H | —C$_2$H$_5$ |
| 13 | —H | —H | n-C$_3$H$_7$ |
| 14 | —H | —H | n-C$_4$H$_9$ |
| 15 | —CONH(CH$_2$)$_2$SO$_2$CH$_2$CH$_2$OH | —H | n-C$_3$H$_7$ |
| 16 | —CONH(CH$_2$)$_2$SO$_2$CH$_2$CH$_2$OH | —H | n-C$_4$H$_9$ |
| 17 | —H | —CONH(CH$_2$)$_2$SO$_2$CH$_2$CH$_2$OH | —C$_2$H$_5$ |
| 18 | —H | —CONH(CH$_2$)$_2$SO$_2$CH$_2$CH$_2$OH | n-C$_3$H$_7$ |
| 19 | —CONH(CH$_2$)$_2$SO$_2$CH$_2$CH$_2$OH | —H | —C$_2$H$_5$ |
| 20 | —CONH(CH$_2$)$_2$SO$_2$CH$_2$CH$_2$OH | —H | —C$_2$H$_5$ |
| 21 | —H | —CONH(CH$_2$)$_2$SO$_2$CH$_2$CH$_2$OH | n-C$_3$H$_7$ |
| 22 | —H | —H | n-C$_3$H$_7$ |
| 23 | —H | —H | n-C$_4$H$_9$ |
| 24 | —CON(CH$_2$CH$_2$SO$_2$CH$_2$CH$_2$OH)$_2$ | —H | n-C$_3$H$_7$ |
| 25 | —CON(CH$_2$CH$_2$SO$_2$CH$_2$CH$_2$OH)$_2$ | —H | n-C$_4$H$_9$ |
| 26 | —H | —H | —C$_2$H$_5$ |
| 27 | —H | —H | —C$_2$H$_5$ |
| 28 | —H | —H | n-C$_3$H$_7$ |
| 29 | —H | —H | —C$_2$H$_5$ |
| 30 | —CH$_2$CH$_2$SO$_2$CH$_2$CH$_2$OH | —H | —C$_2$H$_5$ |

The sulfation of the hydroxy compounds indicated in the table is carried out under the conditions indicated in Examples 4 and 5.

I claim:

1. A process for the preparation of a compound of the formula hydrogen, methyl or ethyl, and m is 2, 3, 4, 5 or 6, s is the number 1 or 2, Z is a radical of the formula —CH$_2$CH$_2$OH, —CH=CH$_2$ or —CH$_2$CH$_2$—Y and Y is —OSO$_3$H, —SSO$_3$H, —OCOCH$_3$, —OCO—C$_6$H$_5$, OPO$_3$H$_2$, —Cl, —Br, —F,

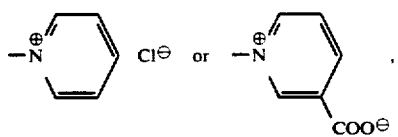

and the benzene or naphthalene nucleus of formula (1) is unsubstituted or substituted by $C_1$-$C_4$alkyl, $C_1$-$C_4$alkoxy, halogen or sulfo, which comprises reacting a compound of the formula

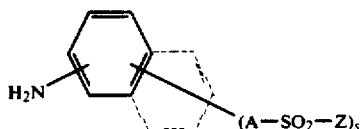
(2)

with a compound of the formula

Q—OH (3)

in which A, s, and Q are as defined under formula (1), in the presence of a platinum, palladium, nickel or copper chromite hydrogenation catalyst and in the absence of a hydrogen atmosphere.

2. A process according to claim 1, in which is used a compound of the formula

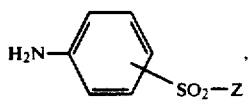
(2a)

in which Z is as defined in claim 1, and the benzene nucleus is unsubstituted or substituted by $C_1$-$C_4$alkyl, $C_1$-$C_4$alkoxy, halogen or sulfo.

3. A process according to claim 1, in which is used a compound of the formula (3) in which Q is $C_1$-$C_4$alkyl.

4. A process according to claim 1, in which Raney nickel is used as hydrogenation catalyst.

5. A process according to claim 1, in which ethanol is used as compound of the formula (3).

6. A process according to claim 1, in which is used a compound of the formula (2) in which Z is β-hydroxyethyl.

7. A process according to claim 1 for the preparation of a compound of the formula

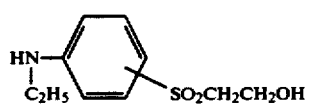
(5)

in which a compound of the formula

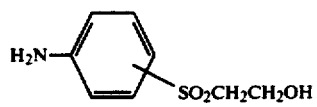
(6)

is reacted with ethanol in the presence of Raney nickel.

8. A process according to claim 1 for the preparation of a compound of the formula

(7)

in which a compound of the formula

(8)

is reacted with ethanol in the presence of Raney nickel.

9. A process according to claim 1, wherein the benzene or naphthalene nucleus of formula (1) is benzene which is not further substituted.

10. A process according to claim 1, wherein the alkylation of the compound of the formula (2) with a compound of the formula (3) is carried out at a temperature between 50° and 250° C. and, at atmospheric or elevated pressure.

11. A process according to claim 10, wherein the alkylation is carried out at a temperature between 100° and 160° C.

12. A process according to claim 10, wherein the alkylation is carried out under a pressure of 1 to 6 bar.

13. A process according to claim 10, wherein the alkylation is carried out under atmospheric pressure at the reflux temperature of the compound of the formula (3).

14. A process according to claim 11, wherein the alkylation is carried out at a temperature between 120° and 140° C.

15. A process according to claim 12, wherein the alkylation is carried out under a pressure of 2.5 to 4.5 bar.

16. A process for the preparation of a compound of the formula

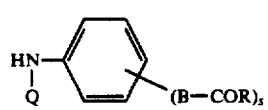
(1b)

in which Q is $C_1$-$C_6$alkyl, s is the number 1 or 2, B is a direct bond or a radical of the formula —$(CH_2)_n$— or —O—$(CH_2)_n$—, n is 1 to 6, R is a radical of the formula

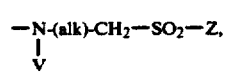
(4a)

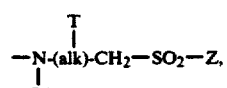
(4b)

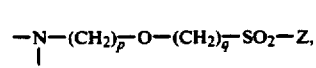
(4c)

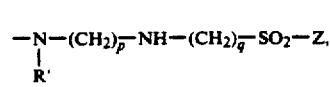
(4d)

-continued

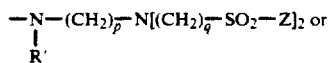 (4e)

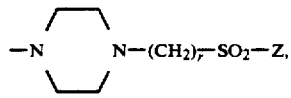 (4f)

in which R' is hydrogen or $C_1$–$C_6$alkyl, (alk) is a $C_1$–$C_6$alkylene radical, T is hydrogen, halogen, hydroxyl, sulfato, carboxyl, cyano, $C_1$–$C_4$alkoxycarbonyl, carbamoyl or a radical —$SO_2$—Z, V is hydrogen, $C_1$–$C_4$alkyl or $C_1$–$C_4$alkyl substituted by halogen, hydroxyl, cyano, carboxyl, sulfo, sulfato, $C_1$–$C_4$alkoxy or $C_1$–$C_4$alkoxycarbonyl, or is a radical of the formula -(alk)-$CH_2$—$SO_2$—Z in which (alk) is as defined above, Z is a radical of the formula —$CH_2CH_2OH$, —$CH=CH_2$ or $CH_2CH_2Y$ and Y is —$OSO_3H$, —$SSO_3H$, —$OCOCH_3$, —OCO—$C_6H_5$, $OPO_3H_2$, —Cl, —Br, —F,

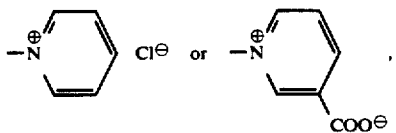

and p, q and r are, independently of one another, an integer from 1 to 6, and the benzene nucleus in formula (1b) is unsubstituted or substituted by $C_1$–$C_4$alkyl, $C_1$–$C_4$alkoxy, halogen or sulfo, which comprises reacting a compound of the formula

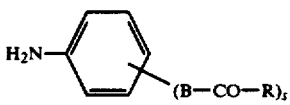 (2b)

with a compound of the formula

Q—OH (3)

in which B, s, and Q are as defined under formula (1), in the presence of a platinum, palladium, nickel or copper chromite hydrogenation catalyst and in the absence of a hydrogen atmosphere.

* * * * *